United States Patent [19]

Renfrew et al.

[11] Patent Number: 5,306,813
[45] Date of Patent: Apr. 26, 1994

[54] REACTIVE DYES HAVING A BULKY LINKER GROUP

[75] Inventors: Andrew H. M. Renfrew, Bury; John A. Taylor, Prestwich, both of England

[73] Assignee: Imperial Chemical Industries PLC, London, England

[21] Appl. No.: 8,084

[22] Filed: Jan. 22, 1993

Related U.S. Application Data

[62] Division of Ser. No. 908,393, Jul. 6, 1992, abandoned.

[30] Foreign Application Priority Data

Jul. 9, 1991 [GB] United Kingdom ............... 9114837

[51] Int. Cl.[5] .................. C09B 62/085; D06P 1/382
[52] U.S. Cl. ................... 534/612; 534/605; 534/606; 534/634; 562/58; 562/458; 564/305
[58] Field of Search .......... 534/605, 606, 612, 634

[56] References Cited

U.S. PATENT DOCUMENTS

| | | | |
|---|---|---|---|
| 2,067,686 | 1/1937 | Semon | 564/305 X |
| 2,323,948 | 7/1943 | Von Bramer et al. | 564/421 X |
| 2,381,015 | 8/1945 | Von Bramer et al. | 564/305 X |
| 2,498,630 | 2/1950 | Thompson | 564/305 X |
| 2,692,288 | 10/1954 | Bell et al. | 564/305 X |
| 3,382,296 | 5/1968 | Tenquist et al. | 564/305 X |
| 3,615,404 | 10/1971 | Price et al. | 564/384 X |
| 4,140,718 | 2/1979 | Symon | 564/398 X |
| 4,453,945 | 6/1984 | Miyamoto et al. | 8/543 |
| 4,966,721 | 10/1990 | Farng et al. | 564/305 X |
| 4,994,238 | 2/1991 | Daffern et al. | 436/170 X |

FOREIGN PATENT DOCUMENTS

| | | | |
|---|---|---|---|
| 458743 | 11/1991 | European Pat. Off. | 534/605 |
| 2525646 | 10/1983 | France . | |
| 2569213 | 2/1986 | France . | |
| 60-86169 | 5/1985 | Japan . | |
| 61-40367 | 2/1986 | Japan | 534/606 |
| 62-30157 | 2/1987 | Japan . | |
| 62-199656 | 9/1987 | Japan . | |
| 1015931 | 1/1966 | United Kingdom . | |
| 1019771 | 2/1966 | United Kingdom | 534/634 |
| 1283771 | 8/1972 | United Kingdom . | |
| 1398601 | 6/1975 | United Kingdom . | |
| 2054662 | 2/1981 | United Kingdom . | |

OTHER PUBLICATIONS

Beech, "Fibre-Reactive Dyes", Logos Press Limited Great Britain 1970 pp. 132–135.
Nagaoka et al, Chemical Abstracts, vol. 93, No. 167890x (1980).

Primary Examiner—Mary C. Lee
Assistant Examiner—Fiona T. Powers
Attorney, Agent, or Firm—Cushman, Darby & Cushman

[57] ABSTRACT

A compound which, in the free acid form, is of Formula (1):

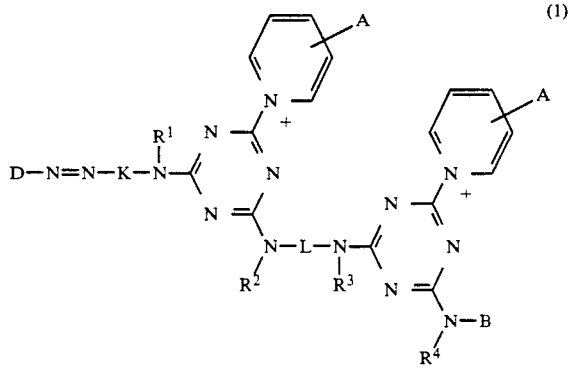

wherein:
D is optionally substituted phenyl or optionally substituted naphthyl;
K is optionally substituted phenylene or optionally substituted naphthylene;
$R^1$ and $R^4$ are each independently H or optionally substituted alkyl;
$R^2$ and $R^3$ are each independently H or optionally substituted alkyl, provided at least one of $R^2$ and $R^3$ is optionally substituted alkyl;
B is H, optionally substituted alkyl or optionally substituted each A is H or a substituent; and each
A is H or a substituent; and
L is an optionally substituted divalent organic radical.
The compound is useful as a reactive dye for textiles.

7 Claims, No Drawings

REACTIVE DYES HAVING A BULKY LINKER GROUP

This is a division of U.S. application Ser. No. 07/908,393, filed on Jul. 6, 1992, now abandoned.

This invention relates to compound suitable for use as reactive dyes, to intermediate compounds therefor and to processes for their manufacture and use. The reactive dyes are suitable for the coloration of a wide variety of substrates having —OH or —NH—groups, and in particular cellulosic materials such as cotton. According to the present invention there is provided a compound which, in the free acid form, is of Formula (1):

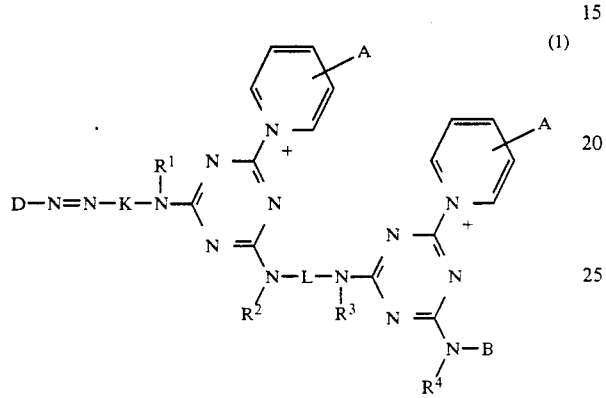

wherein:
D is optionally substituted phenyl or optionally substituted naphthyl;
K is optionally substituted phenylene or optionally substituted naphthylene;
$R^1$ and $R^4$ are each independently H or optionally substituted alkyl;
$R^2$ and $R^3$ are each independently H or optionally substituted alkyl, provided at least one of $R^2$ and $R^3$ is optionally substituted
B is H, optionally substituted alkyl or optionally substituted aryl;
each
A is H or a substituent; and
L is an optionally substituted divalent organic radical.

It is preferred that K is optionally substituted naphthylene. Preferably the total number of sulpho groups on D and K is from 2 to 6.

The optional substituents which may be present on D, K, $R^1$, $R^2$, $R^3$, $R^4$, B, A or L are preferably each independently selected from $C_{1-4}$-alkyl, especially methyl; $C_{1-4}$-alkoxy, especially methoxy; halo, especially Cl; nitro; amino; hydroxy; sulpho; carboxy; ureido; and $C_{1-4}$-amido, especially acetamido.

D preferably has 1, 2 or 3 sulpho substituents. As examples of groups represented by D having 1, 2 or 3 sulpho substituents there may be mentioned 1,5-disulphonaphth-2-yl; 3,6,8-trisulphonaphth-2-yl; 4,8-disulphonaphth-2-yl; 2-sulphophenyl; 3-sulphophenyl, 4-sulphophenyl, 4-methoxy-2-sulphophenyl, 1-sulphonaphth-1-yl, 1,5,7-trisulphonaphth-2-yl, 4-methyl-2-sulphophenyl and 2-methyl-4-sulphophenyl.

When K is an optionally substituted phenylene group it is preferably a 1,4-phenylene which is unsubstituted or substituted by one or two groups selected from sulpho, carboxy, ureido, acetamido and $C_{1-4}$-alkoxy. It is, however, preferred that K is optionally substituted naphthylene, wherein the optional substituents are preferably selected from hydroxy, sulpho, and carboxy. It is especially preferred that K is 1-hydroxy-naphthylene having the group represented by D—N=N—(wherein D is as defined above) attached to the 2-position and the remainder of the molecule shown in Formula (1) is attached to the 6- or 7-position. It is further preferred that K has one or two sulpho groups. Preferred groups represented by D—N=N—K—are of Formula (2) or (3) in which D is as hereinbefore defined and V is H or sulpho.

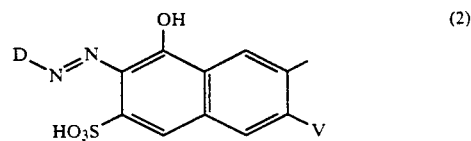

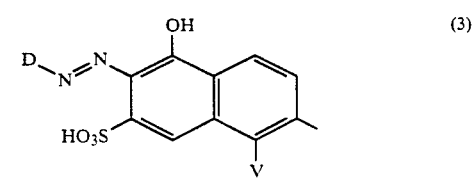

$R^1$ and $R^4$ are preferably each independently H or $C_{1-4}$-alkyl, especially H or methyl. It is especially preferred that $R^1$ and $R^4$ are both methyl.

$R^2$ and $R^3$ are preferably each independently H or $C_{1-4}$-alkyl, provided at least one of $R^2$ and $R^3$ is $C_{1-4}$-alkyl. It is further preferred that both $R^2$ and $R^3$ is $C_{1-4}$-alkyl.

When either of $R^2$ and $R^3$ is $C_{1-4}$-alkyl, it is preferably $C_{2-4}$-alkyl, more preferably $C_{3-4}$-alkyl, especially isopropyl.

B is preferably $C_{1-4}$-alkyl, or more preferably optionally substituted phenyl. The optional substituents which may be present on B are preferably selected from methyl, sulpho and carboxy.

When $R^4$ is H, B is preferably phenyl or sulphophenyl having one or two substituents ortho with respect to the group represented by —$NR^4$—.

Optionally substituted divalent organic radicals represented by L include optionally substituted alkylene, aralkylene and especially optionally substituted arylene radicals. The preferred alkylene radicals represented by L contain from two to seven carbon atoms, the preferred aralkylene radicals contain a phenyl or naphthyl aryl group and a total of up to twelve of carbon atoms, and the preferred optionally substituted arylene radicals are optionally substituted phenylene.

As examples of alkylene and aralkylene radicals represented by L, there may be mentioned:

| | |
|---|---|
| ethylene | 1-chloro-2,3-propylene |
| 1,2- and 1,3-propylene | 1,6- and 2,5-hexylene |
| 2-hydroxy-1,3-propylene | 2,3-diphenyl-1,4-butylene |
| 1- and 2-phenyl-1,3-propylene | 1-(methoxycarbonyl)-1,5-pentylene |
| 2-(4'-sulphophenyl)-1,3-propylene | 1-carboxy-1,5-pentylene |
| 1,4-, 2,3- and 2,4-butylene | 2,7-heptylene |
| 2-methyl-1,3-propylene | 3-methyl-1,6-hexylene |
| 2-methyl-2,4-pentylene | —$CH_2CH_2OCH_2CH_2$— |
| 2,2-dimethyl-1,3-propylene | —$CH_2CH_2SCH_2CH_2$— |
| 1-phenylethylene | —$CH_2CH_2SSCH_2CH_2$— |

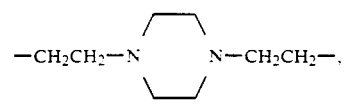

-continued

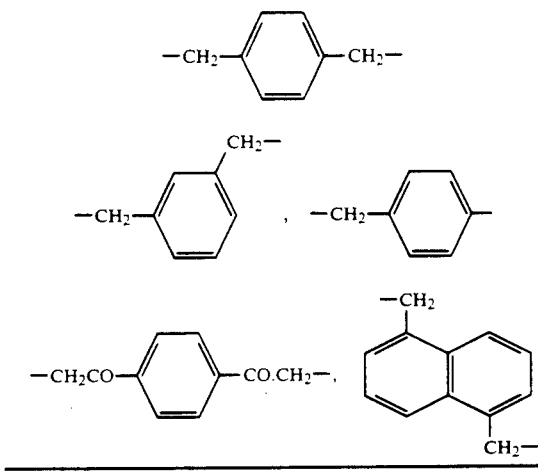

As examples of arylene radicals represented by L, there may be mentioned 1,3- and 1,4-phenylene, 1,4-naphthylene and other divalent radicals containing one or more benzene and/or naphthalene nuclei. Such radicals may optionally contain sulphonic acid groups.

The group represented by A is preferably $CONH_2$, especially carboxy.

The present invention also provides intermediate compounds which can be used to prepare compounds of Formula (1) and a process for the manufacture of such intermediate compounds.

According to a second aspect of the present invention there is provided optionally substituted phenylene dismine compounds having a $C_{2-4}$-alkyl, preferably a $C_{3-4}$-alkyl, especially a $C_3$-alkyl group on each of the amino groups, and use thereof in the preparation of a dye. The optional substituent is preferably carboxy or sulpho. The preferred phenylene dismine compounds of the present invention have said amine groups meta with respect to each other.

Preferred optionally substituted phenylene dismine compounds are of the formula:

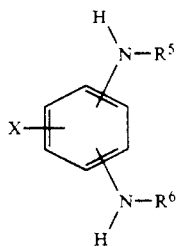

wherein:
$R^5$ and $R^6$ are each independently $C_{2-4}$ alkyl; and X is H, sulpho or carboxy.
$R^5$ and $R^6$ are preferably $C_3$-alkyl. It is preferred that $R^5$ and $R^6$ are identical. X is preferably H.

Preferably the amino groups shown in the above formula are meta- with respect to each other.

A particularly preferred intermediate compound is N,N-diisopropyl-meta-phenylene diamine.

The phenylene diamine compounds having an alkyl group on each of the nitrogen atoms may be prepared by catalytic reduction of the corresponding phenylene diamine compound in the presence of the appropriate alkyl aldehyde or ketone. The appropriate alkylene aldehyde or ketone is selected according to what product is desired, and precisely which alkyl aldehyde or ketone to select will be apparent to those skilled in the art. For example, N,N'-diisopropyl-m-phenylene diamine may be prepared by catalytic reduction of m-phenylene diamine in acetone; the three carbon atoms in the acetone forming the isopropyl substituent by condensation and reduction.

The catalytic reduction is preferably carried out at a high pressure, the preferred catalyst comprises a metal of the platinum group. The catalytic reduction is preferably performed above 100° C., especially in the range 140°–200° C., more especially at around 170° C.

The phenylene diamine is preferably a m-phenylene diamine, and may have a further ring substituent such as sulpho or carboxy, but it is preferred that the phenylene diamine is free from further ring substituents.

The phenylene diamine compounds having different alkyl groups on each of the nitrogen atoms may be prepared in a similar manner to that described above, except that one of the amino groups is first protected, for example using an acyl group such as acetyl, and the resultant mono protected phenylene diamine is catalytically reduced in the presence of an appropriate alkyl aldehyde or ketone, the protecting group is then removed (e.g. by hydrolysis) and the resultant mono alkylated compounds is similarly alkylated on the free amino group by catalytic reduction in the presence of a different aldehyde or ketone to that which was used in the first instance.

As will be readily understood, the compound of Formula (1) will normally be associated with sufficient negatively charged counter ions, for example an anion of an organic acid or $Cl^-$ or $F^-$, to balance the positive charge shown in Formula (1).

The terms "dye" and "dyes" when used as nouns in this specification are not intended to limit compounds of the invention to compounds intended for use in dyeing.

The compounds of Formula (1) may be prepared by forming the diazonium salt of a compound of formula $D-NH_2$, under normal diazotisation conditions such as treatment with $NANO_2$ under acidic conditions at 0°–5° C., and coupling this with a compound of formula $H-K-NR^1H$, to give an azo compound of formula $D-N=N-K-NR^1H$. Said azo compound may then be condensed with one equivalent of a cyanuric halide, followed by one equivalent of a compound of formula $HR^2N-L-NR^3H$ to give a compound of Formula (4):

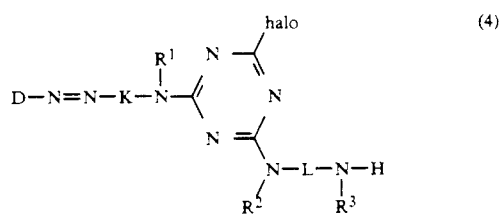

(4)

The compound of Formula (4) may then be condensed with a cyanuric halide followed by one equivalent of an amine of formula $HR^4N-B$, preferably in water, more preferably at a pH of 6–7, especially at a temperature of 15°–40° C. Followed by quaternisation with a pyridine compound substituted by A, to give a compound of Formula (1). Quaternisation is preferably performed in water, especially at a temperature of 50°-105° C., more especially at a pH of 6.5-7.5. In the above process D, K, $R^1$, $R^2$, $R^3$, $R^4$, L, B, x and A are as defined above.

The compounds of Formula (1) can be isolated from the medium in which they have been prepared by conventional methods used for isolation of water-soluble dyes, e.g. by salting out followed by filtration and drying by spray drying the reaction mixture. If desired, stabilizers such as alkali metal hydrogen phosphates or diluents such as sodium chloride or urea can be added. The dyes may also be desalinated using techniques such as reverse osmosis and/or ultrafiltration to give formulations having high solubility in water.

According to a further aspect of the present invention there is provided a composition comprising water and 10% to 50% by weight of a compound of Formula (1). Preferably the compound of Formula (1) is completely dissolved in the water.

Although compounds of Formula (1) have been shown in their free-acid form in this specification, it is intended that the formulae include salts of the compounds, and in particular the alkali metal salts such as the sodium, potassium, lithium or mixed sodium/lithium salt.

A further feature of the present invention provides a process for the coloration of a substrate by applying thereto a compound of Formula (1).

The compounds of Formula (1) can be applied to a wide variety of substrates, particularly those having —OH or —NH—groups, and are especially valuable as dyes for cellulosic materials such as cotton, jute, hemp and flax. The dyes may be applied using standard exhaustion dyeing methods but using little salt. Typically the compound is applied in conjunction with an acid binding agent, e.g. an alkali metal carbonate or bicarbonate, at a temperature of 30° C. to 90° C. The dyes of the present invention are useful for dyeing textiles over a range of liquor ratios, even low liquor ratios of 5:1, and are particularly notable for their high fixation on cellulose and easy wash-off.

The invention is further illustrated but not limited by the following Examples in which all parts and percentages are by weight unless otherwise indicated.

EXAMPLE 1

Preparation of the compound of Formula

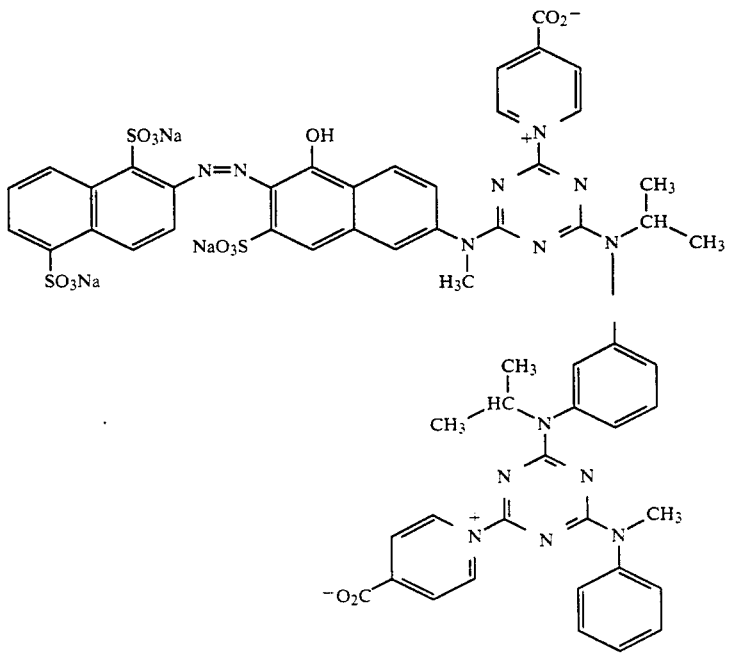

(a) Preparation of N,N'-diisopropyl-m-phenylene diamine. m-Phenylene diamine (216 g) was dissolved in acetone (1200 ml) and carbon treated. 1% Platinum on carbon (5 g) was added and the mixture hydrogenated at 170° C. and 400 lb/sq.m pressure of hydrogen. After the hydrogen uptake had ceased, catalyst was filtered off. Further acetone was added up to a total volume of 2500 ml followed by conc.hydrochloric acid with stirring. The resulting crystalline solid was collected, washed with acetone and dried. Yield 262 g.

Found: C 53.8; H 8.5; N 9.8; Cl 27.5%. $C_{12}H_{20}N_2.2HCl$ requires: C 54.3; H 8.3; N 10.5; Cl 26.8%.

(b) To a stirred aqueous acetone solution (100 ml) of 2-sulpho-3-(1,5-disulphonaphthyl-2-azo)-4-hydroxy-7-[N-(4,6-dichloro-s-triazin-2-yl)-N-methyl]aminonaphthalene (6.36 g) was added N,N1-di-isopropyl-m-phenylene diamine (3.96 g) and the pH adjusted to 7.5. The reaction mixture was heated at 30° C. for 16 hours. The pH of the solution was lowered to 5.0 and NaCl (5 g) added to give a precipitate, which was collected by filtration and washed with brine.

(c) The above precipitate (6 g) was stirred in water (100 ml), and cyanuric chloride (2 g) was added and the reaction mixture stirred at pH 6-7 for 3 hours. The reaction mixture was then filtered, N-methyl-aniline (3 ml) added and stirring continued for a further 16 hours. The resultant product was isolated by drowning the mixture into ethanol (1 liter) and collecting the solid so formed by filtration.

(d) The above solid was converted into the corresponding quaternary iso-nicotinic analogue by stirring with iso-nicotinic acid at 80° C. and pH 7, then finally isolated by salting with sodium chloride to give the title product having a lambda max at approximately 684 nm.

When applied to cotton by exhaust dyeing using little salt the compound gave bright orange shades and displayed good build-up and very easy wash-off.

EXAMPLE 2

The method of Example 1 may be repeated except that in place of N,N'-diisopropyl-m-phenylenediamine there is used N,N'-dimethyl-1,2-ethylenediamine, in place of 2-sulpho-3-(1,5-disulphonaphthyl-2-azo)-4-hydroxy-7-[N-(4,6-dichloro-s-triazin-2-yl)-N-methyl-]aminonaphthalene there is used 2-sulpho-3-(2-sulpho-phenylazo)-4-hydroxy-7-[N-(4,6-dichloro-s-triazin-2-yl)-N-methyl]aminonaphthalene and in place of isonicotinic acid there is used nicotinic acid, to give a dye having a yellow-orange shade.

EXAMPLE 3

The method of Example 1 may be repeated except that in place of 2-sulpho-3-(1,5-disulphonaphthyl-2-azo)-4-hydroxy-7-[N-(4,6-dichloro-s-triazin-2-yl)-N-methyl]aminonaphthalene there is used 2-sulpho-3-(2,4-disulphophenylazo)-4-hydroxy-7-[N-(4,6-dichloro-s-triazin-2-yl)-N-methyllaminonaphthalene to give a dye having a yellow-orange shade.

EXAMPLE 4

The method of Example 1 may be repeated except that in place of N,N'-diisopropyl-m-phenylenediamine there is used N-methyl-1,3-diaminopropane, in place of 2-sulpho-3-(1,5-disulphonaphthyl-2-azo)-4-hydroxy-7-[N-(4,6-dichloro-s-triazin-2-yl)-N-methyl]aminonaphthalene there is used 2-sulpho-3-(2-sulpho-4-methoxy-phenylazo)-4-hydroxy-7-[N-(4,6-dichloro-s-triazin-2-yl)-N-methyl]aminonaphthalene and in place of N-methylaniline acid there is used N-ethylaniline, to give a dye having a scarlet shade.

EXAMPLE 5

The method of Example 1 may be repeated except that in place of N,N'-diisopropyl-m-phenylenediamine there is used N-methyl-N'-isopropyl-m-phenylenediamine, in place of 2-sulpho-3-(1,5-disulpho naphthyl-2-azo)-4-hydroxy-7-[N-(4,6-dichloro-s-triazin-2-yl)-N-methyl] aminonaphthalene there is used 2-sulpho-3-(2-sulpho-4-methylphenylazo)-4-hydroxy-7-[N-(4,6-dichloro-s-triazin-2-yl)-N-methyl}aminonaphthalene and in place of isonicotinic acid there is used pyridine-3-carboxamide, to give a dye having an orange shade.

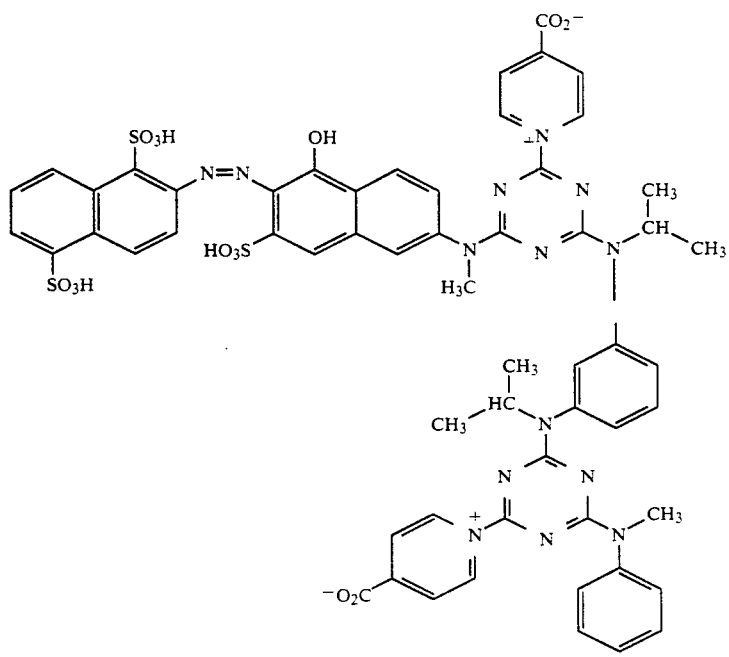

We claim:

1. A compound which, in the free acid form, is of Formula (1):

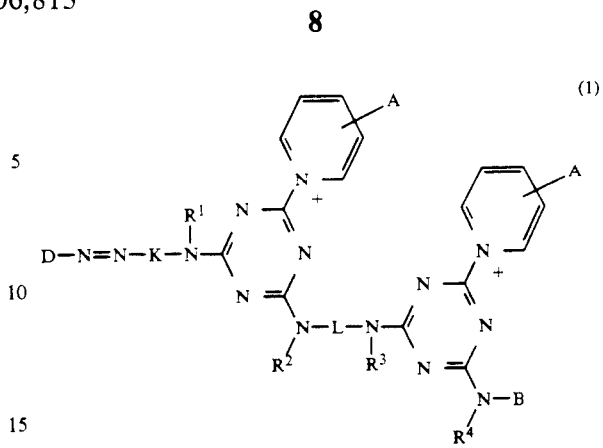

wherein:
D and K are optionally substituted naphthyl;
$R^1$ and $R^4$ are each independently $C_{1-4}$-alkyl;
$R^2$ and $R^3$ are each independently optionally substituted alkyl;
B is optionally substituted aryl;
each
A is 4-carboxy; and
L is an optionally substituent divalent organic radical.

2. A compound according to claim 1 wherein $R^2$ and $R^3$ are each independently $C_{2-4}$-alkyl.

3. A compound according to claim 1 wherein $R^2$ and $R^3$ are isopropyl.

4. A compound according to claim 1 wherein L is optionally substituted phenylene.

5. A compound which, in the free acid form, is of Formula (1):

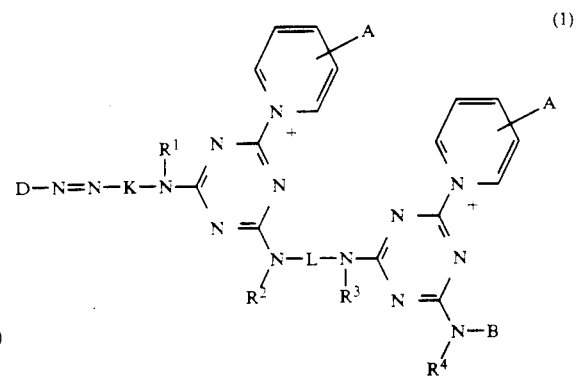

wherein:
D is naphthyl having 1, 2 or 3 sulpho substituents;
K is naphthylene having a substituent selected from hydroxy, sulpho and carboxy;
$R^1$ and $R^4$ are each independently $C_{1-4}$-alkyl;
$R^2$ and $R^3$ are each independently $C_3$-alkyl;
B is H, $C_{1-4}$-alkyl, phenyl or phenyl having a substituent selected from methyl, sulpho and carboxy;
each A 4-carboxy; and
L is phenylene.

6. A compound according to claim 5 wherein $R^2$ and $r^3$ are each are both isopropyl.

7. A compound of the following formula and salts thereof: